United States Patent
Scotto

(10) Patent No.: US 9,399,617 B2
(45) Date of Patent: Jul. 26, 2016

(54) CONCENTRATION OF THE UREA SOLUTION IN A PROCESS FOR THE SYNTHESIS OF UREA

(71) Applicant: Casale SA, Lugano (CH)

(72) Inventor: Andrea Scotto, Breganzona (CH)

(73) Assignee: Casale SA (CH)

( * ) Notice: Subject to any disclaimer, the term of this patent is extended or adjusted under 35 U.S.C. 154(b) by 0 days.

(21) Appl. No.: 14/417,679

(22) PCT Filed: Jul. 3, 2013

(86) PCT No.: PCT/EP2013/064045
§ 371 (c)(1),
(2) Date: Jan. 27, 2015

(87) PCT Pub. No.: WO2014/016090
PCT Pub. Date: Jan. 30, 2014

(65) Prior Publication Data
US 2015/0218089 A1    Aug. 6, 2015

(30) Foreign Application Priority Data
Jul. 27, 2012 (EP) .................................... 12178262

(51) Int. Cl.
C07C 273/16 (2006.01)
C07C 273/04 (2006.01)
B01J 19/24 (2006.01)

(52) U.S. Cl.
CPC ............... *C07C 273/16* (2013.01); *B01J 19/24* (2013.01); *B01J 2219/24* (2013.01); *C07C 273/04* (2013.01)

(58) Field of Classification Search
CPC ............................ C07C 273/04; C07C 273/16
USPC ........................................................ 564/70, 73
See application file for complete search history.

(56) References Cited

U.S. PATENT DOCUMENTS

| | | | | |
|---|---|---|---|---|
| 4,157,348 A * | 6/1979 | Ono | ....................... | C07C 273/04 564/241 |
| 5,053,538 A * | 10/1991 | Linton | .................. | C07C 273/16 564/65 |
| 6,538,157 B1 * | 3/2003 | Goorden | ............... | C07C 273/04 564/66 |
| 9,266,745 B2 * | 2/2016 | Casara | ................. | B01D 61/364 |

* cited by examiner

*Primary Examiner* — Kamal Saeed
*Assistant Examiner* — Janet L Coppins
(74) *Attorney, Agent, or Firm* — Akerman LLP

(57) ABSTRACT

A process and a related plant for the synthesis of urea, where a solution (13) comprising urea is obtained in a synthesis section (10), said solution is treated in a recovery section (14), and an aqueous solution (15) comprising mainly urea and water, which is obtained from said recovery section, is concentrated by means of contact with a water-selective membrane.

11 Claims, 1 Drawing Sheet

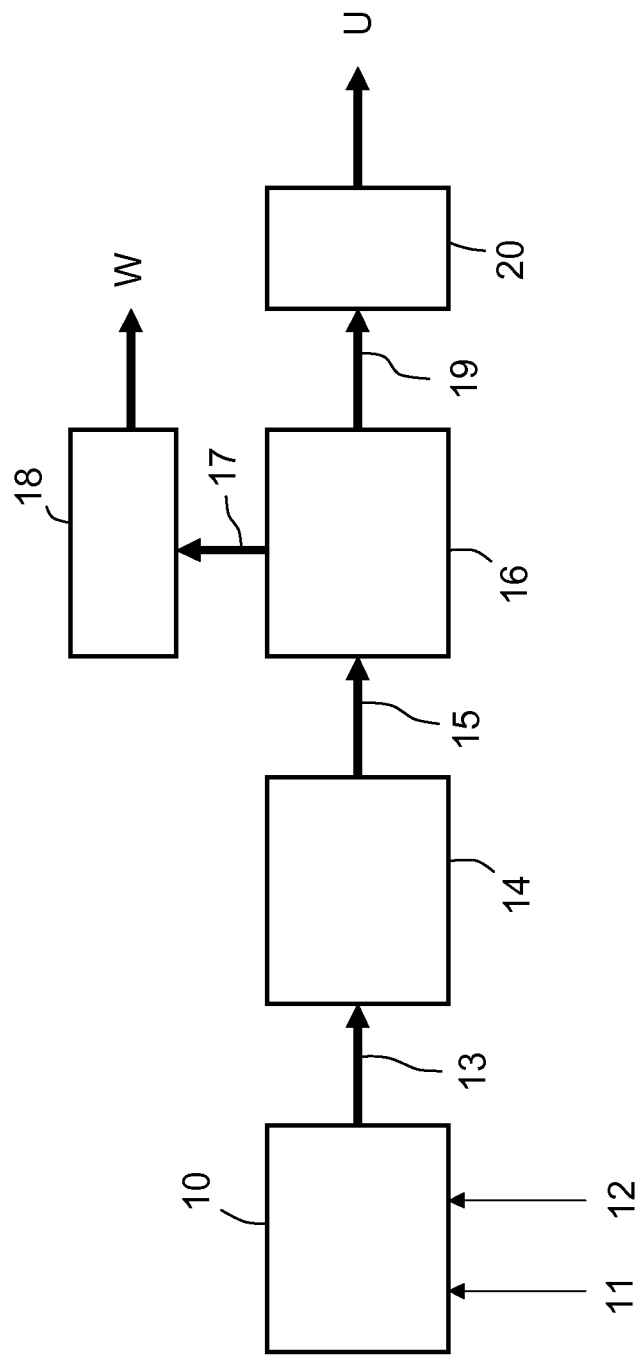

CONCENTRATION OF THE UREA SOLUTION IN A PROCESS FOR THE SYNTHESIS OF UREA

This application is a national phase of PCT/EP2013/064045, filed Jul. 3, 2013, and claims priority to EP 12178262.7, filed Jul. 27, 2012, the entire contents of both of which are hereby incorporated by reference.

FIELD OF THE INVENTION

The present invention refers to the field of synthesis of urea. More in detail, the present invention relates to the step of concentration of the aqueous solution of urea which is obtained from the recovery section of a urea plant.

PRIOR ART

Known processes for the synthesis of urea involves basically a high-pressure synthesis loop, a medium-pressure and/or low-pressure recovery section, a concentration section and a finishing section. An ammonia feed and a carbon dioxide feed are reacted in the synthesis loop, forming a solution of urea, water and ammonium carbamate; this solution is treated in the downstream MP/LP section substantially to recover ammonia and carbon dioxide from dissociation of the carbamate.

The effluent of the recovery section is typically an aqueous solution of urea containing around 50%-90% weight urea, usually 70% to 80% weight in modern plants. For some uses, however, a much higher concentration is required. For example the finishing techniques of prilling and granulation, for converting urea into a solid product, require a urea melt with a purity of 95-99.8% weight. This higher concentration is achieved in the prior art with either vacuum concentration or crystallization of the urea solution.

The above general description is applicable to most of the current facilities for production of urea, in particular to the self-stripping processes and to the CO2-stripping processes as well, and for the design of new urea plants. A discussion of the processes and related plants for production of urea can be found in the literature, e.g. Kirk-Othmer, Encyclopedia of Chemical Technology, $3^{rd}$ Ed, Vol 23, p. 548-562 or Ullmann's, Encyclopedia of Industrial Chemistry, Wiley-VCH Verlag.

It should be noted that a recurring problem in the urea processes is to remove water from the effluent of the HP loop or recovery section, since one mol of water is produced for each mol of urea. As stated above, the need to concentrate the effluent of the recovery section is currently performed with evaporation or crystallization.

Crystallization involves a physical separation between a solid phase (crystallized urea) and a liquid phase (water) and has the drawback of big and complex equipments requiring significant maintenance efforts either in terms of manpower and financial expenditures. Vacuum evaporators have also some drawbacks. First, they need large and expensive vessels, due to their low (vacuum) pressure. Equipments running under vacuum also pose a problem of sealing, to avoid infiltration of air from the outside.

Another drawback is the poor energy efficiency. A vacuum evaporator requires a heat input, which is generally furnished by hot steam produced elsewhere in the plant; furthermore the vacuum is pulled through steam ejectors which are quite inefficient equipment. However, the gaseous effluent from the evaporator along with the ejectors' motive steam must be condensed, discharging a less valuable heat which is no more reusable in the process. Typically said heat is removed by air cooling or water cooling and therefore dissipated to the atmosphere. Hence there is the need to provide a better way to concentrate the urea solution coming from the recovery section of the known urea plants.

SUMMARY OF THE INVENTION

The invention proposes to separate water and possibly other components other than urea, which are contained in the urea solution from recovery section of a urea plant, by means of selective membrane separation.

Accordingly, a first aspect of the invention is a process for the synthesis of urea, where an aqueous solution comprising urea with some residual ammonia and carbon dioxide is obtained in a synthesis section, said solution is treated in a recovery section, and an aqueous solution comprising mainly urea and water, which is obtained from said recovery section, is subject to a process of concentration, characterized in that said process of concentration includes at least a step of selective membrane separation.

Said step of selective membrane separation is carried out with one or more membrane(s). A membrane for carrying out the invention has a first permeability for the transport of water and/or for the transport of other contaminants, and a second and different permeability for the transport of urea. Preferably said step is carried out at least with a water-selective membrane, adapted to separate water from urea and concentrate the solution. For example, a suitable water-selective membrane is permeable to water, and essentially impermeable to other constituents of the solution, namely urea. It can be understood that, for example, when an aqueous solution of urea is contacted with the feed side of a water-selective membrane, water is collected from the discharge side, thus increasing the concentration of the solution at the feed side.

A membrane provides separation between a first side (feed side) and a second side (discharge side). To this purpose, said membrane can be a flat membrane or have a different shape, e.g. spirally wound membrane. Pressure on the feed side and discharge side may be different, in some embodiments, to enhance the process.

The membrane-based concentration can be the only technique of concentration or not. The aqueous solution can be concentrated with a different technique (e.g. evaporation or crystallization) before or after said step of selective membrane separation.

According to different embodiments, the aqueous solution which is subjected to selective membrane separation is the solution as it comes from the recovery section, or a solution previously concentrated with a conventional technique, such as evaporation or crystallization. In the same way, the concentrated solution released by the membrane-based process can be (optionally) further concentrated with another technique if necessary or appropriate.

In some embodiments, said process of concentration includes the use of more than one selective membrane and possibly of several membranes of a different nature, for removal of water and other contaminants of the aqueous solution of urea. Said contaminants may include ammonia or salts such as carbonates, which can be found in small amounts in the solution.

Preferably, the concentration of the incoming solution to the membrane is 50 to 90% wt (by weight) of urea. Preferably, the solution after concentration contains more than 85% wt. urea and more preferably between 95% wt. and 100% wt.

Another aspect of the invention is a plant for the synthesis of urea, comprising a synthesis section and a recovery section, and characterized by a concentration section for treatment of aqueous solution of urea, said concentration section comprising at least a membrane concentration stage comprising a selective membrane. Preferably said membrane is a water-selective membrane for separation of water from aqueous solution of urea.

Another aspect of the invention is the revamping of an existing urea plant, where an existing concentration section is revamped with a membrane-based concentration stage.

The membrane-based separation can replace, totally or partially, a conventional vacuum evaporation or crystallization section. A high concentration can be achieved, such as 95-99.5% wt. or more, suitable for granulation or prilling finishing techniques, without the expensive and large vacuum equipments of the conventional sections. Furthermore, the membrane-based concentration does not need a significant energy or heat input to the benefit of the energy efficiency of the overall process.

DESCRIPTION OF A PREFERRED EMBODIMENT

FIG. 1 shows a block scheme of an embodiment of the invention. The reference 10 denotes a high-pressure synthesis section where ammonia 12 and carbon dioxide 11 are reacted. Said section 10 may comprise, in some embodiments, a reactor, a stripper and a condenser forming a high-pressure loop, according to known art.

The effluent 13 of the section 10 is processed in a recovery section 14, essentially to recover ammonia and carbon dioxide. The aqueous urea solution 15 from the recovery section 14 is sent to a concentration section 16 including a water-selective membrane.

The solution 15, for example, is admitted to a first side of the membrane, and a flow 17 composed mainly of water is obtained at the other side (discharge side) of the membrane. Said flow 17 is preferably treated in a section 18 to obtain substantially pure water W. The concentrated solution 19, having e.g. a concentration around 95-99.5% wt. or more, is passed to a finishing section 20 to obtain a substantially pure urea U.

The invention claimed is:

1. A process for the synthesis of urea, where a solution comprising urea is obtained in a synthesis section where ammonia and carbon dioxide are reacted, said solution is treated in a recovery section, and an aqueous solution comprising mainly urea and water, which is obtained from said recovery section, is subject to a process of concentration, wherein said process of concentration includes a step of selective membrane separation.

2. The process according to claim 1, said step of selective membrane separation being carried out with at least a water-selective membrane.

3. The process according to claim 1, the aqueous solution from the recovery section being concentrated with another process before or after said step of selective membrane separation.

4. The process according to claim 1, said step of selective membrane concentration being carried out with a plurality of membranes.

5. The process according to claim 4, said step of selective membrane concentration being carried out with a plurality of membranes of a different nature for removal of water and other contaminants of the aqueous solution of urea.

6. A plant for the synthesis of urea, comprising a synthesis section, a recovery section and a concentration section for removing water from an aqueous solution of urea discharged by the recovery section, wherein said concentration section includes at least a selective membrane.

7. A plant according to claim 6, wherein said concentration section includes a water-selective membrane.

8. The plant according to claim 7, wherein said water-selective membrane is permeable to water and substantially impermeable to other constituents of the aqueous solution;
said membrane provides separation between a feed side and a discharge side of the membrane; an aqueous solution of urea is admitted to said feed side of the membrane, and a flow composed mainly of water is obtained at said discharge side.

9. A method for revamping a urea plant, the urea plant comprising a synthesis section where ammonia and carbon dioxide are reacted, a recovery section, and a concentration section for removing water from an aqueous solution of urea discharged by the recovery section, the method of revamping being characterized by the provision, in the concentration section, of at least a selective membrane for separation of water and/or other contaminants from aqueous solution of urea.

10. The process according to claim 3, the aqueous solution from the recovery section being concentrated with evaporation or crystallization before or after said step of selective membrane separation.

11. The process according to claim 5, said step of selective membrane concentration being carried out with a plurality of membranes of ammonia and/or carbonates for removal of water and other contaminants of the aqueous solution of urea.

* * * * *